(12) United States Patent
Ebright

(10) Patent No.: US 9,839,634 B2
(45) Date of Patent: Dec. 12, 2017

(54) ANTIBACTERIAL AGENTS: COMBINATION OF A RIFAMYCIN AND A SWITCH REGION INHIBITOR

(71) Applicant: Rutgers, The State University of New Jersey, New Brunswick, NJ (US)

(72) Inventor: Richard H. Ebright, New Brunswick, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 289 days.

(21) Appl. No.: 14/376,789

(22) PCT Filed: Feb. 5, 2013

(86) PCT No.: PCT/US2013/024765
§ 371 (c)(1),
(2) Date: Aug. 5, 2014

(87) PCT Pub. No.: WO2013/119564
PCT Pub. Date: Aug. 15, 2013

(65) Prior Publication Data
US 2015/0031640 A1    Jan. 29, 2015

Related U.S. Application Data

(60) Provisional application No. 61/595,488, filed on Feb. 6, 2012.

(51) Int. Cl.
| | | |
|---|---|---|
| *A61K 31/496* | (2006.01) | |
| *A61K 31/366* | (2006.01) | |
| *A61K 31/395* | (2006.01) | |
| *A61K 31/70* | (2006.01) | |
| *A61K 31/7048* | (2006.01) | |

(52) U.S. Cl.
CPC .......... *A61K 31/496* (2013.01); *A61K 31/366* (2013.01); *A61K 31/395* (2013.01); *A61K 31/70* (2013.01); *A61K 31/7048* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith | |
| 4,608,392 A | 8/1986 | Jacquet | |
| 4,820,508 A | 4/1989 | Wortzman | |
| 4,938,949 A | 7/1990 | Borch | |
| 4,992,478 A | 2/1991 | Geria | |
| 8,114,583 B2 | 2/2012 | Ebright et al. | |
| 8,772,332 B2 | 7/2014 | Ebright et al. | |
| 2005/0187170 A1* | 8/2005 | Bantia | A61K 31/409 514/34 |
| 2006/0127905 A1 | 6/2006 | Ebright | |
| 2006/0246479 A1 | 11/2006 | Ebright | |
| 2006/0269485 A1 | 11/2006 | Friedman et al. | |
| 2007/0292355 A1 | 12/2007 | Tamarkin et al. | |
| 2008/0299220 A1 | 12/2008 | Tamarkin et al. | |
| 2009/0137467 A1 | 5/2009 | Ebright et al. | |
| 2010/0227935 A1 | 9/2010 | Leonetti et al. | |
| 2010/0311074 A1 | 12/2010 | Ebright | |
| 2015/0011647 A1 | 1/2015 | Ebright et al. | |
| 2015/0051275 A1 | 2/2015 | Ebright et al. | |
| 2015/0197512 A1 | 7/2015 | Ebright et al. | |

FOREIGN PATENT DOCUMENTS

| | | |
|---|---|---|
| WO | WO 2005/001034 A2 | 1/2005 |
| WO | WO 2005/024040 A2 | 3/2005 |
| WO | WO 2007/094799 A1 | 8/2007 |
| WO | WO 2012/033815 A1 | 3/2012 |
| WO | WO 2012/033846 A1 | 3/2012 |
| WO | WO 2012/037508 A2 | 3/2012 |

OTHER PUBLICATIONS

Berenbaum, "A method for testing for synergy with any number of agents", *J. Infect. Dis.* 137, 122-130 (1978).
Binder et al., "Emerging infectious diseases: public health issues for the 21st century", *Science* 284, 1311-1313 (1999).
Campbell et al., "Structural mechanism for rifampicin inhibition of bacterial rna polymerase", *Cell* 104, 901-912 (2001).
Floss et al., "Rifamycin-mode of action, resistance, and biosynthesis", *Chem. Rev.* 105, 621-632 (2005).
Hall et al., "Fluctuation analysis CalculatOR: a web tool for the determination of mutation rate using Luria-Delbruck fluctuation analysis", *Bioinformatics* 25, 1564-1565 (2009).
Ho et al., "Structures of RNA polymerase—antibiotic complexes", *Current Opinion in Structural Biology* 19, 715-723 (2009).
Jones, "Accounting for plating efficiency when estimating spontaneous mutation rates", *Mutat. Res.* 292, 187-189 (1993).
Ma et al., "Analysis of the Luria-Delbruck Distribution Using Discrete Convolution Powers", *J. Appl. Probab.* 29, 255-267 (1992).
Mariani et al., "Bacterial RNA polymerase inhibitors: an organized overview of their structure, derivatives, biological activity and current clinical development status", *Curr Med Chem* 16, 430-454 (2009).

(Continued)

*Primary Examiner* — Layla Berry
*Assistant Examiner* — Bahar Craigo
(74) *Attorney, Agent, or Firm* — Viksnins Harris Padys Malen LLP

(57) ABSTRACT

It has been determined that co-administration of a rifamycin and a switch-region inhibitor 1) results in synergistic antibacterial effects, enabling efficacy at low, subtoxic doses, and/or 2) results in a low spontaneous resistance frequency, enabling treatment of high-titer infections without treatment failure due to spontaneous resistance. Accordingly, certain embodiments provide a composition comprising a rifamycin and a switch region inhibitor, as well as methods of use thereof.

7 Claims, 2 Drawing Sheets

(56) References Cited

OTHER PUBLICATIONS

Mukhopadhyay et al., "The RNA Polymerase "Switch Region" is a Target for Inhibitors", *Cell* 135, 295-307 (2008).
Norden et al., "Comparison of techniques for measurement of in vitro antibiotic synergism", *J. Infect. Dis.* 140, 629-633 (1979).
Patent Cooperation Treaty, International Searching Authority, Search Report and Written Opinion for PCT/US13/24765, 10 pages, dated Apr. 9, 2013.
Raviglione et al., "The burden of drug-resistant tuberculosis and mechanisms for its control", *Ann. NY Acad. Sci.* 953, 88-97 (2001).
Sarkar et al., "On fluctuation analysis: a new, simple and efficient method for computing the expected number of mutants", *Genetica* 85, 173-179 (1992).
Schluger, "The Impact of drug resistance on the global tuberculosis epidemic", *Int. J. Tuberculosis Lung Disease* 4, S71-S75 (2000).
Srivastava et al., "New target for inhibition of bacterial RNA polymerase: 'switch region'", *Curr. Opin. Microbiol.* 14, 532-543 (2011).
Stewart et al., "Fluctuation analysis: the probability distribution of the number of mutants under different conditions", *Genetics* 124, 175-815 (1990).
Tallarida, "Drug synergism: its detection and applications", *J. Pharmacol. Exp. Ther.* 298, 865-872 (2001).
Tallarida, "The interaction index: a measure of drug synergism", *Pain* 98, 163-168 (2002).
Villain-Guillot et al., "Progress in targeting bacterial transcription", *Drug Discov Today* 12, 200-208 (2007).
Walsh, "Molecular mechanisms that confer antibacterial drug resistance", *Nature* 406 775-781 (2000).

\* cited by examiner

ANTIBACTERIAL AGENTS: COMBINATION OF A RIFAMYCIN AND A SWITCH REGION INHIBITOR

CROSS-REFERENCE TO RELATED APPLICATION(S)

This patent application claims the benefit of priority of U.S. Application Ser. No. 61/595,488, filed Feb. 6, 2012, which application is herein incorporated by reference.

GOVERNMENT FUNDING

The invention described herein was made with government support under Grant Numbers AI072766 and AI090837 awarded by the National Institutes of Health. The United States Government has certain rights in the invention.

BACKGROUND OF THE INVENTION

Bacterial infections remain among the most common and deadly causes of human disease. Infectious diseases are the third leading cause of death in the United States and the leading cause of death worldwide (Binder et al. (1999) *Science* 284, 1311-1313). Drug-resistant bacteria now cause infections that pose a grave and growing threat to public health. It has been shown that bacterial pathogens can acquire resistance to first-line and even second-line antibiotics (Walsh, C. (2000) *Nature* 406, 775-781; Schluger, N. (2000) *Int. 1. Tuberculosis Lung Disease* 4, S71-S75; Raviglione et al., (2001) *Ann. NY Acad. Sci.* 953, 88-97).

The rifamycin antibacterial agents (e.g., rifampin, rifapentine, rifabutin, rifamixin, and rifalazil) function by inhibiting bacterial RNA polymerase (RNAP), the enzyme responsible for bacterial RNA synthesis (Campbell et al., (2001) *Cell* 104:901-912; Floss et al. (2005) *Chem Rev* 105:621-632; Villain-Guillot et al. (2007) *Drug Discov Today* 12:200-208; Mariani et al. (2009) *Curr Med Chem* 16:430-454; Ho et al. (2009) *Curr Opin Struct Biol* 19:715-723). Rifamycins bind to a site on bacterial RNAP adjacent to the RNAP active center and sterically prevent extension of RNA chains. The rifamycins have an exceptionally broad spectrum of antibacterial activity reflecting the conservation of RNAP across Gram-positive and Gram-negative bacterial species. The rifamycins have exceptional antibacterial activity against non-replicating bacteria, slowly replicating, and biofilm-resident bacteria, reflecting the requirement for low levels of RNAP activity for maintenance of the ability to recover from non-replicating and slowly replicating states. The rifamycins are first-line anti-tuberculosis agents, and are the most effective antituberculosis agents in killing non-replicating tuberculosis bacteria. However, the clinical utility of rifamycins is limited by hepatotoxicity that prevents administration of rifamycins at the concentrations that yield highest bacteriocidal kinetics. The clinical utility also is limited by a relatively high frequency of spontaneous resistance (spontaneous resistance frequency of $\sim 6 \times 10^{-8}$). Resistance to rifamycins typically involves substitution of residues in or adjacent to the rifamycin binding site on RNAP—i.e., substitutions that directly decrease binding of rifamycins.

A new drug target within RNAP, the "switch region", recently was identified, along with compounds, "switch region inhibitors," that inhibit RNAP through the new drug target (Mukhopadhyay et al. (2008) *Cell* 135:295-307; Srivastava et al. (2011) *Curr Opin Microbiol* 14:532-543; WO 05/001034; U.S. Publication 2006-0127905; U.S. Publication 2006-0246479; and WO 07/094799, which are herein incorporated by reference). The switch region is a structural element that mediates opening of the RNAP active-center cleft to bind the DNA template and mediates closing of the RNAP active-center cleft to retain the DNA template. Compounds that bind to the switch region can interfere with opening or closing of the RNAP active-center cleft and can inhibit RNAP allosterically. Since the switch region is conserved across both Gram-positive and Gram-negative bacterial species, inhibitors that function through the switch region typically inhibit RNAP from a broad spectrum of Gram-positive and Gram-negative bacterial species. Since the switch region does not overlap the rifamycin binding site, inhibitors that function through the switch region typically exhibit no cross-resistance with rifamycins.

Four classes of compounds that bind to the switch region, inhibit bacterial RNAP, and exhibit broad-spectrum antibacterial activity have been identified: myxopyronins, corallopyronins, ripostatins, and lipiarmycins (also referred to as tiacumicins and clostomicins). Myxopyronins, corallopyronins, and ripostatins bind to a subregion of the switch region comprising the segment termed "switch 1" and the C-terminal part of the segment termed "switch 2"; this subregion is termed the "SW1/SW2 subtarget." Lipiarmycins bind to an adjacent, but substantially non-overlapping, subregion of the switch region comprising the N-terminal part of the segment termed "switch 2" and the segment termed "switch 3"; this subregion is termed the "SW2/SW3 subtarget."

Myxopyronins are currently in preclinical development for use in antibacterial therapy. Novel myxopyronin derivatives that exhibit potent antibacterial activity against a broad-spectrum of Gram-positive and Gram-negative bacteria in vitro, and that exhibit bioavailability upon systemic or oral administration have been synthesized.

Lipiarmycins are currently in clinical use in antibacterial therapy (under the trade names fidaxomicin and Dificid).

Like rifamycins, switch-region inhibitors, including myxopyronins and lipiarmycins, exhibit relatively high frequencies of spontaneous resistance (e.g., spontaneous resistance frequencies of $\sim 3 \times 10^{-8}$ to $\sim 6 \times 10^{-8}$). Resistance to switch-region inhibitors involves substitution of residues in or adjacent to the switch region—i.e., substitutions that directly decrease binding of switch-region inhibitors.

Accordingly, new therapeutic treatments that are useful in the prevention and treatment bacterial infections are needed. Additionally, new approaches to drug development are necessary to combat the ever increasing number of antibiotic-resistant pathogens.

SUMMARY OF CERTAIN EMBODIMENTS OF THE INVENTION

Compositions that are useful in the prevention and treatment bacterial infections are described herein.

As described herein, it has been discovered that: (1) co-administration of a rifamycin and a switch-region inhibitor results in synergistic antibacterial activity, enabling efficacy at low, subtoxic doses; and (2) co-administration of a rifamycin and a switch-region inhibitor results in a very low spontaneous resistance frequency, enabling treatment of high-titer infections without treatment failure due to spontaneous resistance.

It is disclosed that, in experiments with *Staphylococcus aureus*, the co-administration of rifampin and the switch-region inhibitor myxopyronin B resulted in a >2-fold reduction in minimal inhibitory concentrations and resulted in a >10,000-fold reduction in spontaneous resistance frequencies.

It is further disclosed that, in experiments with *Staphylococcus aureus*, the co-administration of rifampin and the switch-region inhibitor lipiarmycin A3 resulted in a >2-fold reduction in minimal inhibitory concentrations and resulted in a >10,000-fold reduction in spontaneous resistance frequencies.

It is further disclosed that, in experiments with *Escherichia coli*, the co-administration of rifampin and the switch-region inhibitor myxopyronin B resulted in a >100- to >1,000-fold reduction in spontaneous resistance frequencies and a >100- to >1,000-fold reduction in resistance rates.

Accordingly, certain embodiments of the invention provide a composition comprising a rifamycin and a switch region inhibitor.

In certain embodiments, the composition inhibits a bacterial RNA polymerase.

In certain embodiments, the composition inhibits bacterial growth.

In certain embodiments, the composition treats a bacterial infection in a mammal (e.g., human).

In certain embodiments, the combination of the rifamycin and a switch region inhibitor reduces the minimum effective dose of at least one of the rifamycin and the switch region inhibitor.

In certain embodiments, the combination of the rifamycin and a switch region inhibitor reduces the spontaneous resistance frequency to at least one of the rifamycin and the switch region inhibitor.

In certain embodiments, the composition treats an infection in a mammal (e.g., human) without treatment failure due to spontaneous resistance.

DETAILED DESCRIPTION

Figure 1:
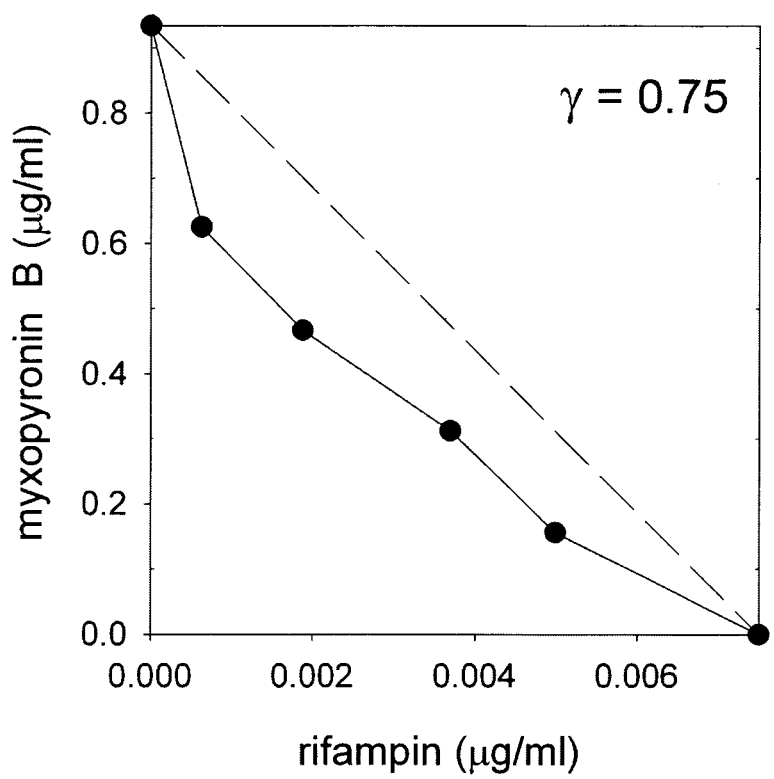
FIG. 1. Isobologram for the co-administration of rifampin and myxopyronin B. All isobologram points for the co-administration of rifampin and myxopyronin B are located below the diagonal, indicating the co-administration of rifampin and myxopyronin B results in super-additive, synergistic antibacterial activity. MIC is the minimum inhibitory concentration. γ is the interaction index (defined as in Tallarida, R. (2002) *Pain* 98:163-168).

It is noted herein that rifamycins and switch-region inhibitors bind to bacterial RNA polymerase (RNAP) through different, independent binding sites, and inhibit RNAP through different, independent mechanisms. As proposed herein, a rifamycin and a switch-region inhibitor will be able to bind to RNAP simultaneously and to inhibit RNAP simultaneously.

Additionally, as proposed herein:

(1) Co-administration of a rifamycin and a switch-region inhibitor will result in super-additive, synergistic antibacterial activity. This will enable high bacteriocidal efficacy and fast bacteriocidal kinetics at low, sub-toxic doses.

(2) Co-administration of a rifamycin and a switch-region inhibitor will result in a very low spontaneous resistance frequency: theoretically $\sim 4 \times 10^{-15}$ (the product of the individual spontaneous resistance frequencies for the rifamycin and the switch-region inhibitor, $\sim 6 \times 10^{-8}$ and $\sim 6 \times 10^{-8}$). This will enable treatment of high-titer infections without treatment failure due to spontaneous resistance.

These proposals have been validated in in vitro experiments with the Gram-positive bacterium *Staphylococcus aureus* and the Gram-negative bacterium *Escherichia coli*, as follows (see Examples):

(1) Co-administration of rifampin and the switch-region inhibitor myxopyronin B resulted in synergistic antibacterial activity (Example 1). In vitro, in experiments with *Staphylococcus aureus*, the minimal inhibitory concentrations of rifampin and myxopyronin B administered together were significantly lower than the minimal inhibitory concentrations of rifampin and myxopyronin B administered individually.

(2) Co-administration of rifampin and the switch-region inhibitor myxopyronin B reduced spontaneous resistance to undetectable levels (Example 2). In vitro, in experiments with *Staphylococcus aureus*, the spontaneous resistance frequency for rifampin and myxopyronin B administered together was more than four orders of magnitude lower than the spontaneous resistance frequencies for rifampin and myxopyronin B administered individually: $<1 \times 10^{-12}$ vs. $6 \times 10^{-8}$ and $6 \times 10^{-8}$). In vitro, in experiments with *Escherichia coli*, the spontaneous resistance frequency for rifampin and myxopyronin B administered together was more than two orders of magnitude lower than the spontaneous resistance frequencies for rifampin and myxopyronin B administered individually: $<1 \times 10^{-12}$ vs. $4 \times 10^{-9}$ and $8 \times 10^{-10}$).

(3) Co-administration of rifampin and the switch-region inhibitor lipiarmycin A3 resulted in synergistic antibacterial activity (Example 3). In vitro, in experiments with *Staphylococcus aureus*, the minimal inhibitory concentrations of rifampin and lipiarmycin A3 administered together were significantly lower than the minimal inhibitory concentrations of rifampin and lipiarmycin A3 administered individually.

(4) Co-administration of rifampin and the switch-region inhibitor lipiarmycin A3 reduced spontaneous resistance to undetectable levels (Example 4). In vitro, in experiments with *Staphylococcus aureus*, the spontaneous resistance frequency for rifampin and lipiarmycin A3 administered together was more than four orders of magnitude lower than the spontaneous resistance frequencies for rifampin and lipiarmycin A3 administered individually: $<1 \times 10^{-12}$ vs. $6 \times 10^{-8}$ and $3 \times 10^{-8}$).

Accordingly, certain embodiments of the invention provide a composition comprising a rifamycin and a switch region inhibitor.

Rifamycins are a class of antibiotics known in the art (for example, see WO 07/089310, pages 3-5 and 9, which is herein incorporated by reference). This class of compounds includes, for example, rifamycin A, rifamycin B, rifamycin C, rifamycin D, rifamycin E, rifamycin S, and rifamycin SV. Additionally, derivatives of rifamycins are known in the art and include, for example, rifampin (rifampicin), rifapentine, rifabutin, rifamixin, and rifalazil.

As used herein, the term "rifamycin" includes compounds from the rifamycin class and derivatives thereof. In certain embodiments the rifamycin is selected from rifamycin A, rifamycin B, rifamycin C, rifamycin D, rifamycin E, rifamycin S, rifamycin SV, rifampin (rifampicin), rifapentine, rifabutin, rifamixin, rifalazil, and pharmaceutically acceptable salts thereof. In certain embodiments, the rifamycin is rifampin or a pharmaceutically acceptable salt thereof.

Switch region inhibitors are known in the art (for example, see Mukhopadhyay et al. (2008) *Cell* 135:295-307; Srivastava et al. (2011) Curr. Opin. Microbiol. 14:532-543); WO 05/001034; U.S. Publication 2006-0127905; U.S. Publication 2006-0246479; and WO 07/094799; which are herein incorporated by reference). Switch region inhibitors include, for example, myxopyronins (e.g., myxopyronin A and myxopyronin B), corallopyronins (e.g., corallopyronin A and corallopyronin A'), ripostatins (e.g., ripostatin A and ripostatin B), and lipiarmycins (also referred to as tiacumicins and clostomicins) (e.g., lipiarmycin A3, lipiarmycin A4, lipiarmycin B3, lipiarmycin B4, and fidaxomicin). Additionally, derivatives of switch region inhibitors are known in the art and include, for example, 7-desmethyl-myxopyronin B, O2'-desmethyl-18-deshydroxy-lipiarmycin A3, O2'-desmethyl-18-deshydroxy-18-methyl-lipiarmycin A3, and didescholoro-lipiarmycin A3.

As used herein, the phrase "switch region inhibitor" includes compounds from the switch region inhibitor class and derivatives thereof. In certain embodiments, the switch region inhibitor is selected from a myxopyronin, a corallopyronin, a ripostatin, and a lipiarmycin (i.e., a tiacumicin or a clostomicin), and pharmaceutically acceptable salts thereof. In certain embodiments, the switch region inhibitor is a myxopyronin or a lipiarmycin (i.e., a tiacumicin or a clostomicin), or pharmaceutically acceptable salts thereof. In certain embodiments, the myxopyronin is selected from myxopyronin A, myxopyronin B, and 7-desmethyl-myxopyronin B, and pharmaceutically acceptable salts thereof. In certain embodiments, the corallopyronin is selected from corallopyronin A and corallopyronin A', and pharmaceutically acceptable salts thereof. In certain embodiments, the ripostatin is selected from ripostatin A and ripostatin B, and pharmaceutically acceptable salts thereof. In certain embodiments, the lipiarmycin is selected from lipiarmycin A3, lipiarmycin A4, lipiarmycin B3, lipiarmycin B4, fidaxomicin, O2'-desmethyl-18-deshydroxy-lipiarmycin A3, O2'-desmethyl-18-deshydroxy-18-methyl-lipiarmycin A3, and didescholoro-lipiarmycin A3, and pharmaceutically acceptable salts thereof. In certain embodiments, the switch region inhibitor is myxopyronin B or a pharmaceutically acceptable salt thereof. In certain embodiments, the switch region inhibitor is lipiarmycin A3 or a pharmaceutically acceptable salt thereof.

In certain embodiments, a composition as described herein inhibits a bacterial RNA. polymerase.

As described herein, a bacterial RNA polymerase may be from, for example, a Gram-positive bacterium (e.g., *Staphylococcus aureus* or *Mycobacterium tuberculosis*) or a Gram-negative bacterium (e.g., *Escherichia coli*). As described herein, a bacterial polymerase may be from, for example, *Staphylococcus aureus*, *Mycobacterium tuberculosis*, or *Escherichia coli*.

In certain embodiments, a composition as described herein inhibits bacterial growth of, for example, a Gram-positive bacterium (e.g., *Staphylococcus aureus* or *Mycobacterium tuberculosis*) or a Gram-negative bacterium (e.g., *Escherichia coli*).

In certain embodiments, a composition as described herein treats or prevents a bacterial infection in a mammal (e.g., human).

As described herein, a bacterial infection may be caused by, for example, a Gram-positive bacterium (e.g., *Staphylococcus aureus* or *Mycobacterium tuberculosis*) or a Gram-negative bacterium (e.g., *Escherichia coli*). As described herein, a bacterial infection may be caused by, for example, *Staphylococcus aureus*, *Mycobacterium tuberculosis*, or *Escherichia coli*.

In certain embodiments, a composition as described herein reduces the minimum effective dose of at least one of the rifamycin and the switch region inhibitor.

In certain embodiments, a composition as described herein reduces the spontaneous resistance of, for example, a Gram-positive bacterium (e.g., *Staphylococcus aureus* or *Mycobacterium tuberculosis*) or a Gram-negative bacterium (e.g., *Escherichia coli*), to at least one of the rifamycin and the switch region inhibitor.

In certain embodiments, a composition as described herein treats or prevents an infection in a mammal (e.g., human) without treatment failure due to spontaneous resistance.

Certain embodiments of the invention provide a composition as described herein further comprising a pharmaceutically acceptable diluent or carrier.

Certain embodiments of the invention provide a method of treating a bacterial infection in a mammal (e.g., human) comprising co-administering 1) a rifamycin and 2) a switch region inhibitor to the mammal.

In certain embodiments, the mammal (e.g., human) is in need of treatment. In certain embodiments, a therapeutically effective amounts of a rifamycin and a switch region inhibitor is co-administered to the mammal.

Certain embodiments of the invention provide a method to reduce the minimum effective dose of at least one of a rifamycin and a switch region inhibitor in a mammal (e.g., human) comprising co-administering 1) the rifamycin and 2) the switch region inhibitor to the mammal.

In certain embodiments, co-administration of a rifamycin and a switch-region inhibitor results in a reduction in the minimal inhibitory concentrations of the rifamycin and the switch region inhibitor, as compared to the minimal inhibitory concentrations of the rifamycin and the switch region inhibitor administered individually. In certain embodiments, co-administration of a rifamycin and a switch-region inhibitor results in a ≥2-fold reduction in the minimal inhibitory concentration of one of the rifamycin and the switch region inhibitor and a >2-fold reduction in the minimal inhibitory concentration of the other of the rifamycin and the switch region inhibitor, as compared to the minimal inhibitory concentrations of the rifamycin and the switch region inhibitor administered individually. In certain embodiments, co-administration of a rifamycin and a switch-region inhibitor results in a ≥2-fold reduction in the minimal inhibitory concentration of one of the rifamycin and the switch region inhibitor and a >4-fold reduction in the minimal inhibitory concentration of the other of the rifamycin and the switch region inhibitor, as compared to the minimal inhibitory concentrations of the rifamycin and the switch region inhibitor administered individually. In certain embodiments, co-administration of a rifamycin and a switch-region inhibitor results in a ≥2-fold reduction in the minimal inhibitory concentration of one of the rifamycin and the switch region inhibitor and a >8-fold reduction in the minimal inhibitory concentration of the other of the rifamycin and the switch region inhibitor, as compared to the minimal inhibitory concentrations of the rifamycin and the switch region inhibitor administered individually.

Certain embodiments of the invention provide a method to reduce the spontaneous resistance frequency to at least one of a rifamycin and a switch region inhibitor in a mammal (e.g., human) comprising co-administering 1) the rifamycin and 2) the switch region inhibitor to the mammal.

In certain embodiments, the spontaneous resistance frequency for a rifamycin and a switch region inhibitor administered together is less than the spontaneous resistance frequencies for the rifamycin and the switch region inhibitors administered individually. In certain embodiments, co-administration of a rifamycin and a switch-region inhibitor results in a >100-fold reduction in spontaneous resistance frequencies. In certain embodiments, co-administration of a rifamycin and a switch-region inhibitor results in a >1,000-fold reduction in spontaneous resistance frequencies. In certain embodiments, co-administration of a rifamycin and a switch-region inhibitor results in a >10,000-fold reduction in spontaneous resistance frequencies.

Certain embodiments of the invention provide a method to treat a bacterial infection in a mammal (e.g., human) without treatment failure due to spontaneous resistance comprising co-administering 1) a rifamycin and 2) a switch region inhibitor to the mammal.

In certain embodiments, a composition comprising the rifamycin and the switch region inhibitor is administered.

Certain embodiments of the invention provide a method for inhibiting a bacterial RNA polymerase comprising contacting the bacterial RNA polymerase in vitro or in vivo with 1) a rifamycin and 2) a switch region inhibitor.

Certain embodiments of the invention provide a method for inhibiting the growth of a bacterium comprising contacting the bacterium in vitro or in vivo with 1) a rifamycin and 2) a switch region inhibitor.

In certain embodiments of the invention, the bacterium is a Gram-positive bacterium.

In certain embodiments of the invention, the Gram-positive bacterium is *Staphylococcus aureus*.

In certain embodiments of the invention, the Gram-positive bacterium is *Mycobacterium tuberculosis*.

In certain embodiments of the invention, the bacterium is a Gram-negative bacterium.

In certain embodiments of the invention, the Gram-negative bacterium is *Escherichia coli*.

In certain embodiments of the invention the bacterium is *Staphylococcus aureus, Mycobacterium tuberculosis*, or *Escherichia coli*.

Certain embodiments of the invention provide a composition as described herein for the use in the inhibition of a bacterial RNA polymerase.

Certain embodiments of the invention provide a composition as described herein for use in the inhibition of bacterial growth.

Certain embodiments of the invention provide a composition as described herein for use in the treatment of a bacterial infection.

Certain embodiments of the invention provide a composition as described herein for use in the reduction of the minimum effective dose of at least one of the rifamycin and the switch region inhibitor.

Certain embodiments of the invention provide a composition as described herein for use in the reduction of the spontaneous resistance frequency to at least one of the rifamycin and the switch region inhibitor.

Certain embodiments of the invention provide a composition as described herein for use in the treatment of an infection in a mammal (e.g., human) without treatment failure due to spontaneous resistance.

Certain embodiments of the invention provide a composition as described herein for use in medical therapy.

Certain embodiments of the invention provide the use of a rifamycin and a switch region inhibitor to inhibit a bacterial RNA polymerase.

Certain embodiments of the invention provide the use of a rifamycin and a switch region inhibitor to inhibit bacterial growth.

Certain embodiments of the invention provide the use of a rifamycin and a switch region inhibitor for the treatment of a bacterial infection in a mammal (e.g., human).

Certain embodiments of the invention provide the use of a rifamycin and a switch region inhibitor to reduce the minimum effective dose of at least one of the rifamycin and the switch region inhibitor.

Certain embodiments of the invention provide the use of a rifamycin and a switch region inhibitor to reduce the spontaneous resistance frequency to at least one of the rifamycin and the switch region inhibitor.

Certain embodiments of the invention provide the use of a rifamycin and a switch region inhibitor to treat an infection in a mammal (e.g., human) without treatment failure due to spontaneous resistance.

Certain embodiments of the invention provide the use of a rifamycin and a switch region inhibitor for the manufacture of a medicament useful for inhibiting a bacterial RNA polymerase.

Certain embodiments of the invention provide the use of a rifamycin and a switch region inhibitor for the manufacture of a medicament useful for inhibiting bacterial growth.

Certain embodiments of the invention provide the use of a rifamycin and a switch region inhibitor for the manufacture of a medicament useful for treatment of a bacterial infection in a mammal (e.g., human).

Certain embodiments of the invention provide the use of a rifamycin and a switch region inhibitor for the manufacture of a medicament useful for reducing the minimum effective dose of at least one of the rifamycin and the switch region inhibitor.

Certain embodiments of the invention provide the use of a rifamycin and a switch region inhibitor for the manufacture of a medicament useful for reducing the spontaneous resistance frequency to at least one of the rifamycin and the switch region inhibitor.

Certain embodiments of the invention provide the use of a rifamycin and a switch region inhibitor for the manufacture of a medicament useful for treating an infection in a mammal (e.g., human) without treatment failure due to spontaneous resistance.

Certain embodiments of the invention are directed to a product comprising a rifamycin and a switch region inhibitor as a combined preparation for separate, simultaneous or sequential use in the treatment of a bacterial infection.

The rifamycin and a switch region inhibitor may be co-administered. As used herein, the term "co-administer" refers to administration of two or more agents within a 24 hour period of each other, for example, as part of a clinical treatment regimen. In other embodiments, "co-administer" refers to administration within 2 hours of each other. In other embodiments, "co-administer" refers to administration within 30 minutes of each other. In other embodiments, "co-administer" refers to administration within 15 minutes of each other. In other embodiments, "co-administer" refers to administration at the same time, either as part of a single formulation or as multiple formulations that are administered by the same or different routes.

As used herein, the terms "treat" and "treatment" can refer to therapeutic treatment or to prophylactic or preventative treatment, wherein the object is to prevent or decrease an undesired physiological change or disorder, such as the development or spread of an infection. For the purposes of this invention, beneficial or desired clinical results include, but are not limited to, alleviation of symptoms, diminishment of extent of the infection, stabilized (i.e., not worsening) state of infection, delay or slowing of the progression of the infection, amelioration or palliation of the infection state, and elimination of the infection state. "Treatment" can also mean prolonging survival as compared to expected survival if not receiving treatment. Those in need of treatment may include those already with the infection as well as those in which the infection is to be prevented.

The phrase "therapeutically effective amount" means an amount of a rifamycin and a switch region inhibitor or a composition as described herein that (i) treats or prevents the particular infection, (ii) attenuates, ameliorates, or eliminates one or more symptoms of the particular infection, or (iii) prevents or delays the onset of one or more symptoms of the particular infection.

The term "unit dosage form" refers to a physically discrete unit, such as a capsule, tablet, or solution that is suitable as a unitary dosage for a human patient, each unit containing a predetermined quantity of one or more active ingredient(s) calculated to produce a therapeutic effect, in association with at least one pharmaceutically acceptable diluent or carrier, or combination thereof.

If desired, the effective daily dose of a compound described herein may be administered as two, three, four, five, six, or more sub-doses administered separately at appropriate intervals throughout the day, optionally, in unit dosage forms.

In cases where compounds are sufficiently basic or acidic, a salt of the compound can be useful as an intermediate for isolating or purifying the compound of interest. Additionally, administration of a compound as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The present compounds and compositions can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds and compositions may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the present compounds and compositions to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the present compounds and compositions can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 150 mg/kg, e.g., from about 1.5 to about 50 mg/kg of body weight per day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising the present compound(s) formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following illustrate representative pharmaceutical dosage forms, containing a composition of the invention, for therapeutic or prophylactic use in humans.

| (i) Tablet 1 | mg/tablet |
|---|---|
| Composition | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Composition | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Composition | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/ml |
|---|---|
| Composition (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Composition (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| Composition | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All documents cited herein are incorporated by reference. While certain embodiments of invention are described, and many details have been set forth for purposes of illustration, certain of the details can be varied without departing from the basic principles of the invention.

The use of the terms "a" and "an" and "the" and similar terms in the context of describing embodiments of invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. In addition to the order detailed herein, the methods described herein can be performed in any suitable order unless otherwise indicated herein or otherwise clearly contradicted by context. The use of any and all examples, or exemplary language (e.g., "such as") provided herein, is intended merely to better illuminate embodiments of invention and does not necessarily impose a limitation on the scope of the invention unless otherwise specifically recited in the claims. No language in the specification should be construed as indicating that any non-claimed element is essential to the practice of the invention.

The invention will now be illustrated by the following non-limiting Examples.

EXAMPLES

Example 1

Co-Administration of Rifampin and the Switch-Region Inhibitor Myxopyronin B Results in Synergistic Antibacterial Activity Compound-compound interactions were assessed in "checkerboard"-format broth-microdilution antibacterial susceptibility assays essentially as described [Berenbaum, M. (1978) A method for testing for synergy with any number of agents. J. Infect. Dis. 137, 122-130; Norden, C., Wentzel, H. & Keleti, E. (1979) Comparison of techniques for measurement of in vitro antibiotic synergism. J. Infect. Dis. 140, 629-633]. Assays were performed using Staphylococcus aureus ATCC 12600 ($5 \times 10^5$ cfu/well) as the assay organism and Mueller-Hinton Broth II, Cation Adjusted (100 µl/well), as the assay medium, and 14 h at 37° C. as the assay incubation time.

Isobolograms were plotted and interpreted as described [Berenbaum, M. (1978) A method for testing for synergy with any number of agents. J. Infect. Dis. 137, 122-130; Norden, C., Wentzel, H. & Keleti, E. (1979) Comparison of techniques for measurement of in vitro antibiotic synergism. J. Infect. Dis. 140, 629-633; Tallarida, R. (2001) Drug synergism: its detection and applications. J. Pharmacol. Exp. Ther. 298, 865-872; Tallarida, R. (2002) The interaction index: a measure of drug synergism. Pain 98, 163-168]. Isobologram plots above, on, and below the diagonal were indicative of, respectively less-than-additive (antagonistic), additive, and super-additive (synergistic) interactions.

Interactions indices, y, were calculated as described [Tallarida, R. (2002) The interaction index: a measure of drug synergism. Pain 98, 163-168]. Interaction indices of >1, 0, and <0 were indicative of, respectively less-than-additive (antagonistic), additive, and super-additive (synergistic) interactions.

The isobologram is presented in FIG. 1. All isobologram points for the co-administration of rifampin and myxopyronin B were located below the diagonal, indicating the co-administration of rifampin and myxopyronin B resulted in super-additive, synergistic antibacterial activity. Co-administration resulted in a 12-fold reduction in the minimal inhibitory concentration of rifampin and 1.6-fold reduction in the minimal inhibitory concentration of myxopyronin B (second point from left), a 4-fold reduction in the minimal inhibitory concentration of rifampin and 2-fold reduction in the minimal inhibitory concentration of myxopyronin B (third point from left), or a 2-fold reduction in the minimal inhibitory concentration of rifampin and 3-fold reduction in the minimal inhibitory concentration of myxopyronin B (fourth point from left), as compared to the minimal inhibitory concentrations of rifampin and the myxopyronin B administered individually. The interaction index, $\gamma$, was 0.75, indicating super-additive, synergistic interaction.

Example 2

Co-Administration of Rifampin and the Switch-Region Inhibitor Myxopyronin B Reduces Spontaneous Resistance to Undetectable Levels Spontaneous resistance frequencies in Staphylococcus aureus were determined by plating defined numbers of cells of Staphylococcus aureus ATCC12600 ($1 \times 10^8$-$1 \times 10^{12}$ cfu/plate) on Mueller-Hinton agar containing rifampin, myxopyronin B, or both, and counting numbers of colonies after 14 h at 37° C. Experiments were performed using (a) rifampin at 1×, 2×, or 4× the minimum inhibitory concentration of rifampin administered individually; (b) myxopyronin B at 1×, 2×, or 4× the minimum inhibitory concentration of myxopyronin B administered individually; or (c) both rifampin at 1×, 2×, or 4× the minimum inhibitory concentration of rifampin administered individually and myxopyronin B at 1×, 2×, or 4× the minimum inhibitory concentration of myxopyronin B administered individually. All experiments were performed four times, using four different starting cultures.

The results in Table 1 show that the spontaneous resistance frequencies for rifampin alone, myxopyronin B alone, and rifampin co-administered with myxopyronin B were, respectively, $6 \times 10^{-8}$, $6 \times 10^{-8}$, and undetectable ($<1 \times 10^{-12}$).

TABLE 1

Spontaneous resistance frequencies for rifampin, myxopyronin B, and co-administered rifampin and myxopyronin B (Staphylococcus aureus).

| | spontaneous resistance frequency | | |
|---|---|---|---|
| concentration | rifampin | myxopyronin B | rifampin plus myxopyronin B |
| 1×MIC | $5 \times 10^{-8}$ | $4 \times 10^{-8}$ | $<1 \times 10^{-12}$ |
| 2×MIC | $6 \times 10^{-8}$ | $7 \times 10^{-8}$ | $<1 \times 10^{-12}$ |
| 4×MIC | $6 \times 10^{-8}$ | $7 \times 10^{-8}$ | $<1 \times 10^{-12}$ |
| mean | $6 \times 10^{-8}$ | $6 \times 10^{-8}$ | $<1 \times 10^{-12}$ |

Spontaneous resistance frequencies in Escherichia coli were determined by plating defined numbers of cells of Escherichia coli D21f2tolC ($1 \times 10^8$-$1 \times 10^{12}$ cfu/plate) on LB agar containing rifampin, myxopyronin B, or both, and counting numbers of colonies after 24 h at 37° C. Experiments were performed using (a) rifampin at 2× the minimum inhibitory concentration of rifampin administered individually; (b) myxopyronin B at 2× the minimum inhibitory concentration of myxopyronin B administered individually; or (c) both rifampin at 2× the minimum inhibitory concentration of rifampin administered individually and myxopyronin B at 2× the minimum inhibitory concentration of myxopyronin B administered individually. All experiments were performed at least five times, using at least five different starting cultures. Resistance rates and 95% confidence intervals were calculated using the Ma-Sandri-Sarkar Maximum Likelihood Estimator (MSS-MLE; [Ma, W, Sandri, GvH., Sarkar, S. (1992. ) J. Appl. Probab. 29, 255-267; Sarkar, S., Ma, W., Sandri, GvH. (1992) Genetica 85, 173-179]) as implemented on the Fluctuation Analysis Calculator (FALCOR; http://www.keshaysingh.org/protocols/FALCOR.html; [Hall, B., Ma, C., Liang, P., Singh, K (2009) Bioinformatics 25, 1564-1565]). Sampling correction was performed as in [Stewart, F., Gordon, D., Levin, B. (1990) Genetics 124, 175-185; Jones, M. (1993) Mutat. Res. 292, 187-189].

The results in Table 2 show that the spontaneous resistance frequencies for rifampin alone, myxopyronin B alone, and rifampin co-administered with myxopyronin B were, respectively, $4 \times 10^{-9}$, $8 \times 10^{-10}$, and undetectable ($<1 \times 10^{-12}$).

The results in Table 3 show that the resistance rates for rifampin alone, myxopyronin B alone, and rifampin co-administered with myxopyronin B were, respectively, $1 \times 10^{-9}$ per generation, $3 \times 10^{-10}$ per generation, and undetectable ($<1 \times 10^{-12}$ per generation).

TABLE 2

Spontaneous resistance frequencies for rifampin, myxopyronin B, and co-administered rifampin and myxopyronin B (*Escherichia coli*).

| | spontaneous resistance frequency | | |
|---|---|---|---|
| concentration | rifampin | myxopyronin B | rifampin plus myxopyronin B |
| 2×MIC | $4 \times 10^{-9}$ | $8 \times 10^{-10}$ | $<1 \times 10^{-12}$ |

TABLE 3

Resistance rates for rifampin, myxopyronin B, and co-administered rifampin and myxopyronin B (*Escherichia coli*).

| | resistance rate per generation (95% confidence interval) | | |
|---|---|---|---|
| concentration | rifampin | myxopyronin B | rifampin plus myxopyronin B |
| 2×MIC | $1 \times 10^{-9}$ (0.6-2 × $10^{-9}$) | $3 \times 10^{-10}$ (1-7 × $10^{-10}$) | $<1 \times 10^{-12}$ |

Example 3

Figure 2:
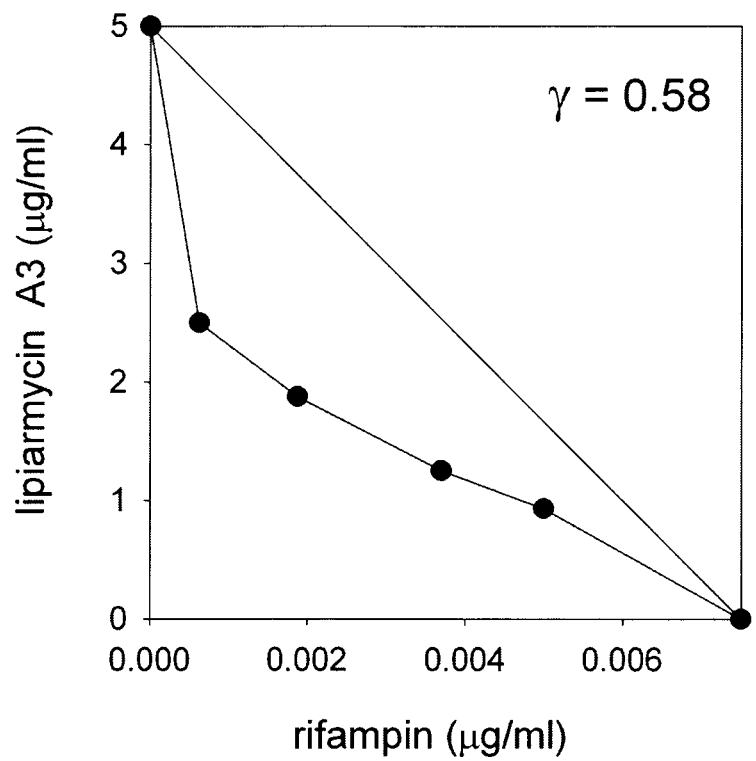
FIG. 2. Isobologram for the co-administration of rifampin and lipiarmycin A3. All isobologram points for the co-administration of rifampin and lipiarmycin A3 are located below the diagonal, indicating the co-administration of rifampin and lipiarmycin A3 results in super-additive, synergistic antibacterial activity. MIC is the minimum inhibitory concentration. γ is the interaction index (defined as in Tallarida, R. (2002) *Pain* 98:163-168).

Co-Administration of Rifampin and the Switch-region Inhibitor Lipiarmycin A3 Results in Synergistic Antibacterial Activity Compound-compound interactions were assessed as in Example 1. The isobologram is presented in FIG. 2. All isobologram points for the co-administration of rifampin and lipiarmycin A3 were located below the diagonal, indicating that the co-administration of rifampin and lipiarmycin A3 resulted in super-additive, synergistic antibacterial activity. Co-administration resulted in a 12-fold reduction in the minimal inhibitory concentration of rifampin and 2-fold reduction in the minimal inhibitory concentration of lipiarmycin A3 (second point from left), a 4-fold reduction in the minimal inhibitory concentration of rifampin and 2.7-fold reduction in the minimal inhibitory concentration of lipiarmycin A3 (third point from left), or a 2-fold reduction in the minimal inhibitory concentration of rifampin and 4-fold reduction in the minimal inhibitory concentration of lipiarmycin A3 (fourth point from left), as compared to the minimal inhibitory concentrations of rifampin and lipiarmycin A3 administered individually. The interaction index, γ, was 0.58, indicating super-additive, synergistic interaction.

Example 4

Co-Administration of Rifampin and the Switch-Region Inhibitor Lipiarmycin A3 Reduces Spontaneous Resistance to Undetectable Levels Spontaneous resistance frequencies in *Staphylococcus aureus* were determined essentially as described in Example 2. The results in Table 4 showed that the spontaneous resistance frequencies for rifampin alone, lipiarmycin A3 alone, and rifampin co-administered with lipiarmycin A3 were, respectively, $6 \times 10^{-8}$, $3 \times 10^{-8}$, and undetectable ($<1 \times 10^{-12}$).

TABLE 4

Spontaneous resistance frequencies for rifampin, myxopyronin B, and co-administered rifampin and lipiarmycin A3 (*Staphylococcus aureus*).

| | spontaneous resistance frequency | | |
|---|---|---|---|
| concentration | rifampin | lipiarmycin A3 | rifampin plus lipiarmycin A3 |
| 2×MIC | $6 \times 10^{-8}$ | $3 \times 10^{-8}$ | $<1 \times 10^{-12}$ |

What is claimed is:

1. A composition comprising a rifamycin and a switch region inhibitor, wherein the switch region inhibitor is a myxopyronin or a lipiarmycin.

2. The composition of claim 1, wherein the rifamycin is selected from rifamycin A, rifamycin B, rifamycin C, rifamycin D, rifamycin E, rifamycin S, rifamycin SV, rifampin (rifampicin), rifapentine, rifabutin, rifamixin, and rifalazil.

3. The composition of claim 2, wherein the rifamycin is rifampin.

4. The composition of claim 1 further comprising a pharmaceutically acceptable diluent or carrier.

5. The composition of claim 1, wherein the switch region inhibitor is a myxopyronin.

6. A composition comprising rifampin and a myxopyronin.

7. A composition comprising rifampin and a lipiarmycin.

* * * * *